United States Patent [19]

Suzuki et al.

[11] Patent Number: 4,835,142

[45] Date of Patent: May 30, 1989

[54] POWDERY PHARMACEUTICAL COMPOSITION SUITABLE FOR APPLICATION TO MUCOSA OF ORAL OR NASAL CAVITY

[75] Inventors: Yoshiki Suzuki; Hiroshi Ikura, both of Hino, Japan

[73] Assignee: Teijin Limited, Osaka, Japan

[21] Appl. No.: 153,527

[22] Filed: Feb. 4, 1988

Related U.S. Application Data

[63] Continuation of Ser. No. 692,091, Jan. 25, 1985, abandoned.

[51] Int. Cl.$^4$ .................. A61K 31/715; A61K 31/56
[52] U.S. Cl. ...................................... 514/53; 514/180
[58] Field of Search ................................. 514/180, 53

[56] References Cited

U.S. PATENT DOCUMENTS

| | | | |
|---|---|---|---|
| 3,276,959 | 10/1966 | Ritter et al. | 167/65 |
| 4,246,040 | 1/1981 | Okamura et al. | 106/308 A |
| 4,289,764 | 9/1981 | Yarrow et al. | 424/243 |
| 4,294,829 | 10/1981 | Suzuki et al. | 514/180 |
| 4,294,852 | 10/1981 | Wildnauer | 514/180 |
| 4,389,393 | 6/1983 | Schor et al. | 514/180 |

FOREIGN PATENT DOCUMENTS 23359  2/1981  European Pat. Off. .

OTHER PUBLICATIONS

Chemical Abstracts; vol. 93 (1980) #179506q; Nasyrov et al.

*Primary Examiner*—Leonard Schenkman
*Assistant Examiner*—Joseph A. Lipovsky
*Attorney, Agent, or Firm*—Sughrue, Mion, Zinn, Macpeak, and Seas

[57] ABSTRACT

A powdery pharmaceutical composition for application to the mucosa of the oral or nasal cavity including: (a) a base selected from the group consisting of lower alkyl ethers of cellulose; (b) a pharmaceutically effective amount of a drug selected from the group consisting of steroid or glycyrrhizic acid type anti-inflammatory agents; and (c) a stabilizer for the drug composed of at least one low irritant solid organic acid selected from the group consisting of saturated higher aliphatic monocarboxylic acids having 12 or more carbon atoms, aliphatic polycarboxylic acid, hydroxy aliphatic polycarboxylic acids, aromatic carboxylic acids, unsaturated lower aliphatic monocarboxylic acids having six or less carbon atoms, and cellulose derivatives having carboxyl group.

This powdery pharmaceutical composition has extremely excellent stability in the steroid or glycyrrhizic acid type anti-inflammatory agent contained therein, low irritation of the mucosa of the oral or nasal cavity, and sustained release of the drug over an extended period of time.

22 Claims, No Drawings

POWDERY PHARMACEUTICAL COMPOSITION SUITABLE FOR APPLICATION TO MUCOSA OF ORAL OR NASAL CAVITY

This is a continuation of application Ser. No. 06/692,091, filed Jan. 25, 1985 now abandoned.

BACKGROUND OF THE INVENTION

1. Field of the Invention

The present invention relates to a powdery pharmaceutical composition suitable for application to the mucosa of the oral or nasal cavity. More specifically, it relates to a powdery pharmaceutical composition, suitable for application to the mucosa of the oral or nasal cavity, containing (a) lower alkyl ethers of cellulose as a base, (b) a steroid or glycyrrhizic acid type anti-inflammatory agent as a drug component, and (c) a solid low irritant organic acid as a stabilizer for the drug component.

The powdery pharmaceutical composition exhibits extremely excellent stability in the steroid or glycyrrhizic acid type anti-inflammatory agent contained therein, low irritation of the mucosa of the oral or nasal cavity, and sustained release of the drug over an extended period of time. Accordingly, the powdery pharmaceutical composition according to the present invention can be effectively used for the treatment of oral diseases such as stomatitis, erosion or sores generated by radiotherapy, and licken planus or nasal diseases such as allergic rhinitis and vasomotor rhinitis.

2. Description of the Related Art

Various pharmaceutical preparations, such as buccal tablets, troche tablets, sublingual tablets, and oral ointments, have been heretofore known in the art for application to the oral cavity. Buccal tablets, troche tablets, and sublingual tablets, however, give a foreign feeling to the oral cavity. Therefore, patients often chew on and swallow the tablets. Oral ointments, on the other hand, usually contain mixtures of beeswax or plastibase with gelatin, pectin, or sodium carboxymethyl cellulose. These mixtures are unsatisfactory because the adhesion properties thereof to the oral mucosa are not sufficient and also because they have unpleasant tastes.

On the other hand, various pharmaceutical preparations, such as nasal ointments, jellies, nose drops, and sprays, have been known in the art for application to the nasal cavity. Nasal ointments and jellies, however, are difficult to apply to deep parts of the nasal cavity, such as the concha nasalis superior. With, nose drops and sprays, the active components do not remain in the nasal cavity for an extended period of time.

Various sustained release pharmaceutical preparations for oral or nasal cavity administration are known in the art. With these, the efficacy of the drugs is spread over a long period of time by the gradual or sustained releasing the active drug components from the pharmaceutical preparations. For example, Japanese Unexamined Patent Publication (Kokai) No. 57-118511 discloses powdery sustained release preparations suitable for adhesion to the oral cavity. These preparations use, as a base, hydroxypropyl cellulose and have the advantages of an excellent sustained release of the drugs and possible application over a wide range of the oral cavity. Furthermore, U.S. Pat. No. 4,294,829 discloses powdery sustained release preparations suitable for application to the nasal cavity. These contain lower alkyl ethers of cellulose and drugs and also have the advantage of excellent sustained release of the drugs.

It is, however, more desirable to improve the stability of drugs in the above-mentioned sustained release preparations for application to the mucosa of the oral or nasal cavity.

SUMMARY OF THE INVENTION

Accordingly, the object of the present invention is to provide a powdery pharmaceutical composition, suitable for application to the mucosa of the oral or nasal cavity, having extremely excellent stability of the carried drug, i.e., a steroid or glycyrrhizic acid type anti-inflammatory agent.

Another object of the present invention is to provide a powdery pharmaceutical composition, suitable for application to the mucosa of the oral or nasal cavity, containing a lower alkyl ether of cellulose as a base, a steroid or glycyrrhizic acid type anti-inflammatory agent as a drug, and a specific solid low irritant organic acid as a stabilizer for the drug.

A further object of the present invention is to provide a powdery pharmaceutical composition having low irritation of the mucosa of the oral or nasal cavity.

A still further object of the present invention is to provide a powdery pharmaceutical composition having excellent sustained release of the drug.

A still further object of the present invention is to provide a powdery pharmaceutical composition having a particle diameter suitable for administration to the oral or nasal cavity.

A still further object of the present invention is to provide a method for preparing a powdery pharmaceutical composition suitable for application to the mucosa of the oral or nasal cavity.

A still further objects of the present invention is to provide a method for stabilizing a powdery pharmaceutical composition containing a steroid or glycyrrhizic acid type anti-inflammatory agent as a drug.

Other objects and advantages of the present invention will be apparent from the following description.

According to the present invention, the above-mentioned objects and advantages can be achieved by a powdery pharmaceutical composition including: (a) a base selected from the group consisting of lower alkyl ethers of cellulose; (b) a pharmaceutically effective amount of a drug selected from the group consisting of steroid or glycyrrhizic acid type anti-inflammatory agents; and (c) a stabilizer for the drug composed of at least one low irritant solid organic acid selected from the group consisting of saturated higher aliphatic monocarboxylic acids having 12 or more carbon atoms, aliphatic polycarboxylic acids, hydroxy aliphatic polycarboxylic acids, aromatic carboxylic acids, unsaturated lower aliphatic monocarboxylic acids having six or less carbon atoms, and cellulose derivatives having carboxyl groups.

DESCRIPTION OF THE PREFERRED EMBODIMENTS

According to the present invention, the desired powdery pharmaceutical composition, i.e., a composition having extremely excellent stability of the drug, low irritation to the mucosa of the oral or nasal cavity, and excellent sustained release of the drug, can be obtained by using a lower alkyl ether of cellulose as a base, a steroid or glycyrrhizic acid type anti-inflammatory agent as a drug, and a specific solid low irritant organic acid as a stabilizer for the drug, i.e., by combining the specified base and the specified drug wtih the specified organic acid.

The lower alkyl ethers of cellulose usable as a base in the present invention are those obtained by at least partially substituting the same or different lower alkyl ether groups for a plurality of hydroxyl groups of cellulose. The lower alkyl groups in the lower alkyl ether groups may be substituted with substituents. An example of such preferable substituents is a hydroxyl group.

Preferable examples of the optionally substituted lower alkyl groups are a methyl group, and hydroxy lower alkyl groups having 2 or 3 carbon atoms.

Examples of the optionally substituted lower alkyl groups are methyl, ethyl, n-propyl, iso-propyl, β-hydroxyethyl, and β-hydroxypropyl.

Examples of the optionally substituted lower alkyl ethers of cellulose are methyl cellulose, hydroxyethyl cellulose, hydroxypropyl cellulose, and hyroxypropylmethyl cellulose. Of these lower alkyl ethers of cellulose, the use of methyl cellulose, hyroxypropyl cellulose, and hydroxypropylmethyl cellulose is preferable due to the facts that these lower alkyl ethers of cellulose have substantially no odor and irritation when applied to the mucosa of the oral or nasal cavity, which is particularly sensitive to odor and irritation, and that the desired sustained release of the drug can be obtained. Of these lower alkyl ethers of cellulose, the use of hydroxypropyl cellulose is especially preferable.

The lower alkyl ethers of cellulose can be used alone or in any mixture thereof.

When the above-mentioned lower alkyl ethers of cellulose are used as a base in the powdery pharmaceutical composition according to the present invention, the pharmaceutical preparations thus obtained can adhere to the mucosa of the oral or nasal cavity and will swell to gradually release the active drug components therefrom over a long period of time. Thus, the affected or diseased parts can be treated by the drugs over a long period of time.

Although there is no limitation in the molecular weight of the lower alkyl ethers of cellulose usable in the present invention, lower alkyl ethers having a viscosity in 2% aqueous solution thereof of 3 to 10,000 cps at 37° C. ±0.2° C., more preferably, 1000 to 4000 cps at 37° C. ±0.2° C., are preferably used.

In preparing unit dosage forms of powdery pharmaceutical compositions in which lower alkyl ethers of cellulose are contained as a base, the compositions are generally filled in hard capsules. These capsules are set in a specially designed spraying device. The spraying device is provided with needle for spraying the powdery pharmaceutical compositions into the oral or nasal cavity. In this case, when the moisture content of the lower alkyl ethers of cellulose in the capsules is too small, the moisture contained in the membranes of the capsules tends to be absorbed by the lower alkyl ethers of cellulose and, as a result, the capsules become too rigid. Therefore, lower alkyl ethers of cellulose having a moisture content of 3% to 9% by weight, especially 4% to 8% by weight, are preferably used as a base.

The drugs usable in the present powdery pharmaceutical compositions are steroid or glycyrrhizic acid type anti-inflammatory agents. Examples of such steroid type anti-inflammatory agents are beclomethasone dipropionate, betamethasone, betamethasone valerate, triamcinolone, triamcinolone acetonide, dexamethasone, fluocinolone acetonide, fluocinonide, flumethasone, hydrocortisone, prednisolone, and prednisone. Examples of glycyrrhizic acid type anti-inflammatory agents are glycyrrhizic acid, disodium glycyrrhizinate, trisodium glycyrrhizinate, monopotassium glycyrrhizinate, dipotassium glycyrrhizinate and monoammonium glycyrrhizinate. These drugs can be used alone or in any mixture thereof in the present powdery pharmaceutical composition.

According to the present invention, the above-mentioned anti-inflammatory agents contained in the powdery pharmaceutical compositions comprising the above-mentioned lower alkyl ethers of cellulose as a base can be advantageously stabilized by incorporating thereinto, as a stabilizer, a specified organic acid, i.e., at least one solid low irritant organic acid selected from the group consisting of saturated higher aliphatic monocarboxylic acids having 12 or more carbon atoms, aliphatic polycarboxylic acids, hydroxy aliphatic polycarboxylic acids, aromatic carboxylic acids, unsaturated lower aliphatic monocarboxylic acids having six or less carbon atoms, and cellulose derivatives having carboxyl groups.

The organic acids usable as a stabilizer for the drug in the present invention are those selected from the above-mentioned group of the organic acids which are solid at room temperature, less irritant to the mucosa of the oral or nasal cavity, and substantially odorless or with only a very slight odor. By the term "organic acids" is meant acids comprising organic groups and free carboxylic groups. Use of the organic acids solid at room temperature facilitates the production of the desired powdery pharmaceutical compositions in a uniform particle size. Use of the less irritant organic acids means higher safety when the composition is applied to the mucosa of the oral or nasal cavity.

Examples of the preferable saturated higher aliphatic monocarboxylic acids are saturated higher aliphatic hydrocarbon monocarboxylic acid having 12 to 24 carbon atoms, such as stearic acid, palmitic acid, lauric acid, and myristic acid. Examples of the preferable aliphatic polycarboxylic acids are aliphatic hydrocarbon dicarboxylic acids having 4 to 6 carbon atoms, such as, succinic acid, fumaric acid, and maleic acid. Examples of the preferable hydroxy aliphatic polycarboxylic acid are hydroxy aliphatic hydrocarbon di- or tri-carboxylic acids having 4 to 8 carbon atoms, such as, tartaric acid and citric acid. Examples of the preferably aromatic acids are benzoic acid and its derivatives, such as parahydroxy benzoic acid and salicylic acid. Examples of the preferable unsaturated lower aliphatic monocarboxylic acids are unsaturated lower aliphatic hydrocarbon monocarboxylic acid having 4 to 6 carbon atoms, such as sorbic acid. Examples of the preferable cellulose derivatives having carboxyl groups are carboxymethyl cellulose and carboxymethylethyl cellulose. These organic acids can be used alone or in any mixture thereof.

Of the above-mentioned organic acids, saturated higher aliphatic monocarboxylic acids having 12 or more carbon atoms, aliphatic polycarboxylic acids, hydroxy aliphatic polycarboxylic acids, aromatic carboxylic acids, and cellulose derivatives having carboxyl groups are preferably used. For powdery pharmaceutical compositions for application to the nasal cavity, use of saturated higher aliphatic monocarboxylic acids having 12 or more carbon atoms and cellulose derivatives having carboxyl groups is especially preferably from the viewpoints of low irritation and substantial odorlessness.

There is no specific limitation in the amount of the above-mentioned organic acids in the present pharmaceutical composition as long as the anti-inflammatory agents are stabilized. The preferable amount of the organic acid in the present pharmaceutical composition is within the range of from 0.05% to 5% by weight, especially from 0.1% to 3% by weight, based upon the total weight of the composition. Although there is also no critical limitation in the particle size of the organic acid, the organic acid preferably has such a particle size that at least about 90% by weight of the powder particles has an effective particle diameter of about 75 $\mu$m or less, more preferably about 20 $\mu$m to about 75 $\mu$m, to obtain a powdery pharmaceutical composition capable of being effectively administered to the mucosa of the oral or nasal cavity.

As mentioned above, the powdery pharmaceutical compositions according to the present invention contain, as essential constituents, the above-mentioned lower alkyl ethers of cellulose, steroid or glycyrrhizic acid type anti-inflammatory agents, and organic acid stabilizers. Although there is no specific limitation is the particle size of the present pharmaceutical composition, the particle size of the present pharmaceutical composition is preferably such that at least about 90% by weight of the powder particles thereof has an effective particle diameter of about 20 $\mu$m to about 250 $\mu$m. The present powdery pharmaceutical composition having such a particle size distribution is preferably due to the fact that the amount of the powder particles adhering to the mucosa of the oral or nasal cavity becomes large. That is, when the pharmaceutical composition having the above-mentioned preferable particle size distribution is applied to the oral or nasal cavity, the amount of the pharmaceutical composition reaching, for example, the lung becomes small or the amount of the pharmaceutical composition scattered out of the oral or nasal cavity becomes small. Furthermore, the pharmaceutical composition having the above-mentioned preferable particle size can well adhere to the mucosa of the oral or nasal cavity and can be effectively and gradually released. The powdery pharmaceutical composition according to the present invention more preferably has such a particle size distribution that at least about 90% by weight of the powder particles has an effective particle diameter of about 20 $\mu$m to abouta 150 $\mu$m.

The term "effective particle diameter" used herein means that determined by the opening sizes of sieves. For example, a powder having an effective diameter (d) of $37 < d \leq 44$ passes through a sieve having an opening size of 44 microns but does not pass through a sieve having an opening size of 37 microns.

A vibratory sieve is used when the effective particle diameter of a powder is more than 37 microns, and a sonic sieve (Micro Hand Sifter SWM-2, a product of Tsutsui Rikagaku Kikai Co., Ltd.) is used when the effective particle diameter of a powder is not more than 37 microns.

The sieves used has an opening size of 500, 420, 350, 297, 250, 210, 177, 149, 125, 105, 88, 74, 63, 53, 44, 37, 25, and 20 microns, respectively.

The powdery pharmaceutical composition according to the present invention can optionally contain, in addition to the above-mentioned lower alkyl ethers of cellulose, anti-inflammatory agents, and organic acids, any conventional ingredients for improving the physical properties, visual appearance, or odor of the pharmaceutical preparations. Examples of such ingredients are: lubricants such as talc and waxes; binders such as starch, dextrin, tragacanth gum, gelatin, polyvinylpyrrolidone, and polyvinyl alcohol; diluents such as starch, crystalline cellulose, dextrin, lactose, mannitol, sorbitol, and anhydrous calcium phosphate; odor improvers such as menthol and citrus perfumes; preservatives such as methyl p-hydroxybenzoate, propyl p-hydroxybenzoate; and various surfactants.

The powdery pharmaceutical composition according to the present invention can be prepared in any conventional manner. For example, the pharmaceutical composition can be prepared by mechanically mixing the above-mentioned three essential constituents, i.e., the lower alkyl ethers of cellulose, the anti-inflammatory agents, and the solid organic acids and the above-mentioned optional ingredients, if any. The mixing of the composition can be carried out by using any conventional means such as ball mills, and V-type mixers. The desired pharmaceutical composition can also be prepared by mechanically mixing all the above-mentioned constituents of the composition, compressing the resultant mixture under pressure, e.g., 0.2 to 0.4 ton, to and pulverizing the compressed mixture so as to obtain the desired particle size distribution. The mixed or pulverized powder particles can be sieved to obtain the powdery composition having the desired particle size distribution, if necessary.

The desired pharmaceutical composition can further be prepared by impregnating the lower alkyl ethers of cellulose with a solution or dispersion, in an organic solvent (e.g., methanol, ethanol, ethyl cellosolve, and dichloromethane), of the anti-inflammatory agents and the organic acids and, if any, the optional ingredients, followed by drying the impregnated product. The said organic solvent may contain water. The impregnation can be carried out by, for example, spraying the above-mentioned solution or dispersion to the lower alkyl ethers of cellulose in the form of powder particles in a spray apparatus. The particle size distribution of the lower alkyl ethers of cellulose can be controlled to the desired range prior to the impregnation. Alternatively, the powder particles of the impregnated product can be pulverized and/or sieved after the impregnation so as to obtain the desired particle size distribution.

Furthermore, the desired pharmaceutical compositions can be prepared by dissolving or dispersing the lower alkyl ethers of cellulose, the anti-inflammatory agents, the solid organic acid, and any optional ingredients in organic solvents such as methanol, ethanol, ethyl cellosolve, and dichloromethane, water, or the mixture thereof followed by evaporating the organic solvents off. The resultant composition can be pulverized and/or sieved to obtain the desired particle size distribution.

According to the present invention, a powdery preparation in a unit dosage form including the above-mentioned powdery pharmaceutical composition can be obtained. The present pharmaceutical composition can be directly converted to the powdery preparation in the form of a unit dosage. The unit dosage of the powdery preparations according to the present invention is preferably about 10 mg to about 400 mg, especially about 30 mg to about 300 mg, when applied to the oral cavity and about 5 mg to about 200 mg, especially about 10 mg to about 100 mg, when applied to the nasal cavity.

The amount of the steroid or glycyrrhizic acid type anti-inflammatory agent in the powdery preparation in the unit dosage form depends upon the pharmaceutically effective amount of the anti-inflammatory agent to be used and the number of dosages of the preparation. For example, when beclomethasone dipropionate is incorporated into the powdery preparations for application to the nasal or oral cavity, the appropriate amount is about 25 to 200 μg/day, although the conventional amount is about 200 to 400 μg/day. When dipotassium glycyrrhizinate is incorporated into the powdery preparations for application to the oral cavity, the appropriate amount is about 0.1 to 15 mg/day, although the conventional amount is about 10 to 30 mg/day. This is because, since lower alkyl ethers of cellulose are used in the present pharmaceutical composition, a desired sustained release of the drug component can be obtained.

The powdery preparations of the present invention can be preferably filled into capsules, such as hard gelatin capsules, as a preferred dosage form.

The present powdery preparations can be advantageously applied to the oral or nasal cavity. For example, a capsule filled with the present powdery preparation is set in a spraying device equipped with a needle. The capsule is pierced with the needle to provide minute holes on the top and bottom sides. The powdery preparation is then sprayed or jetted out from the capsule by sending air into the capsule by means of, for example, a rubber ball.

As mentioned above, when the moisture content in the powdery preparation filled in a hard gelatin capsule is too small, the powdery preparation absorbs moisture from the gelatine membrane. Therefore, water is preferably contained in an amount of 3% to 8.5% by weight, especially 4% to 8.5% by weight, in the lower alkyl ethers of cellulose in the powdery preparations.

The powdery preparations according to the present invention can be widely used for the treatment of oral diseases such as stomatitis, erosion or sores generated by radiotherapy, and lichen planus or nasal diseases such as allergic rhinitis and vasomotor rhinitis.

EXAMPLE

The present invention will now be described in detail with reference to, but is by no means limited to, the following examples, wherein all percentages and parts are on the weight basis unless otherwise specified.

Example 1

A 100 part amount of hydroxypropyl cellulose having a viscosity of a 2% aqueous solution thereof of 1550 cps at 37° C.±0.2° C. and having a particle size such that 90% or more of the powder particles had a particle diameter of 37 to 149 μm was used.

One part of the hydroxypropyl cellulose and 0.025 parts of beclomethasone dipropionate were thoroughly mixed in a mortar and, then, 9 parts of hydroxypropyl cellulose was gradually added thereto. The resultant mixture was thoroughly mixed and, then, the remaining hydroxypropyl cellulose were added and thoroughly mixed in a mixer. Thereafter, 0.5 parts of stearic acid was added and thoroughly mixed.

Thus, a powdery composition for the application to the oral cavity containing beclomethasone dipropionate uniformly dispersed therein was prepared. The powdery composition was filled in #2 hard gelatin capsules in an amount of 200 mg each to prepare a powdery preparation in a unit dosage form for the application to the oral cavity.

Example 2

A powdery preparation in a unit dosage form for the application to the oral cavity was prepared in the same manner as in Example 1, except that palmitic acid was used instead of stearic acid.

Example 3

A powdery preparation in a unit dosage form for the application to the oral cavity was prepared in the same manner as in Example 1, except that citric acid was used instead of stearic acid.

Example 4

A powdery preparation in a unit dosage form for the application to the oral cavity was prepared in the same manner as in Example 1, except that benzoic acid was used instead of stearic acid.

Example 5

A powdery preparation in a unit dosage form for the application to the oral cavity was prepared in the same manner as in Example 1, except that sorbic acid was used instead of stearic acid.

Example 6

Powdery compositions for the application to the oral cavity were prepared in the same manner as in Example 1, except that the amounts of stearic acid were changed to 0, 0.1, 0.3, 0.5, and 0.7 parts. These powdery compositions were filed in #2 hard gelatin capsules in an amount of 200 mg each.

The capsules thus prepared were allowed to stand at a temperature of 60° C. for one month. The residual percentages of beclomethasone dipropionate in the capsules were determined.

The results were as shown in Table 1.

TABLE 1

| Content of stearic acid (%) | 0 | 0.1 | 0.3 | 0.5 | 0.7 |
|---|---|---|---|---|---|
| Residual percent of beclomethasone dipropionate (%) | 75.0 | 89.0 | 95.2 | 97.8 | 99.2 |

Example 7

Powdery compositions for the application to the oral cavity were prepared in the same manner as in Example 2, except that the amounts of palmitic acid were changed to 0, 0.1, 0.3, and 0.5 parts. These powdery compositions were filled in #2 hard gelatin capsules in an amount of 200 mg each.

The capsules thus prepared were allowed to stand at a temperature of 60° C. for one month. The residual percentages of beclomethasone dipropionate in the capsules were determined.

The results were as shown in Table 2.

TABLE 2

| Content of palmitic acid (%) | 0 | 0.1 | 0.3 | 0.5 |
|---|---|---|---|---|
| Residual percentage of beclomethasone dipropionate (%) | 78.5 | 90.0 | 95.2 | 98.1 |

Example 8

Powdery compositions for the application to the oral cavity were prepared in the same manner as in Example 3, except that the amounts of citric acid were changed to 0, 0.05, 0.1, 0.5, 1, and 3 parts. These powdery compositions were filled in #2 hard gelatin capsules in an amount of 200 mg each.

The capsules thus prepared were allowed to stand at a temperature of 60° C. for one month. The residual percentages of beclomethasone dipropionate in the capsules were determined.

The results were as shown in Table 3.

TABLE 3

| Content of citric acid (%) | 0 | 0.05 | 0.1 | 0.5 | 1 | 3 |
|---|---|---|---|---|---|---|
| Residual percentage of beclomethasone dipropionate (%) | 78.5 | 92.0 | 94.3 | 100.0 | 100.0 | 100.0 |

Example 9

Powdery compositions for the application to the oral cavity were prepared in the same manner as in Example 4, except that the amounts of benzoic acid were changed to 0, 0.05, 0.1, and 0.5 parts. These powdery compositions were filled in #2 hard gelatin capsules in an amount of 200 mg each.

The capsules thus prepared were allowed to stand at a temperature of 60° C. for one month. The residual percentages of beclomethasone dipropionate in the capsules were determined.

The results were as shown in Table 4.

TABLE 4

| Content of benzoic acid (%) | 0 | 0.05 | 0.1 | 0.5 |
|---|---|---|---|---|
| Residual percentage of beclomethasone dipropionate (%) | 82.5 | 93.2 | 94.0 | 100.0 |

Example 10

Powdery compositions for the application to the oral cavity were prepared in the same manner as in Example 5, except that the amounts of sorbic acid were changed to 0, 0.1, 0.3, and 0.5 parts. These powdery compositions were filled in #2 hard gelatin capsules in an amount of 200 mg each.

The capsules thus prepared were allowed to stand at a temperature of 60° C. for one month. The residual percentages of beclomethasone dipropionate in the capsules were determined.

The results were as shown in Table 5.

TABLE 5

| Content of sorbic acid (%) | 0 | 0.1 | 0.3 | 0.5 |
|---|---|---|---|---|
| Residual percentage of beclomethasone dipropionate (%) | 83.1 | 92.6 | 98.2 | 98.9 |

Example 11

Powdery preparations for the application to the oral cavity were prepared in the same manner, except that 100 parts of methyl cellulose having a viscosity of a 2% aqueous solution thereof of 1335 cps at 37° C.±0.2° C. and 0.025 parts of triamcinolon acetonide were used and that the amounts of the stearic acid were changed to 0, 0.1, 0.3, and 0.5 parts.

The residual percentages of the triamcinolon acetonide were determined after the capsuled preparations were allowed to stand at a temperature of 60° C. for one month.

The results were as shown in Table 6.

TABLE 6

| Content of stearic acid (%) | 0 | 0.1 | 0.3 | 0.5 |
|---|---|---|---|---|
| Residual percentage of triamcinolone acetonide (%) | 81.0 | 92.6 | 97.8 | 100.0 |

Example 12

A 100 part amount of hydroxypropyl cellulose having a viscosity of a 2% aqueous solution thereof of 1550 cps at 37° C.±0.2° C. and having a particle size such that 90% or more of the powder particles had a particle diameter of 37 to 149 μm was used.

A 10 part amount part of the hydroxypropyl cellulose and 0.17 parts of beclomethasone dipropionate were thoroughly mixed in a mixer and, then, the remaining hydroxypropyl cellulose was gradually added thereto. The resultant mixture was thoroughly mixed. Thereafter, 0.5 parts of stearic acid was added and thoroughly mixed.

Thus, a powdery composition for the application to the nasal cavity containing beclomethasone dipropionate uniformly dispersed therein was prepared. The powdery composition was filled in #2 hard gelatin capsules in an amount of 30 mg each to prepare a powdery preparation in a unit dosage form for the application to the nasal cavity.

Example 13

A 100 part amount of methyl cellulose having a viscosity of a 2% aqueous solution thereof of 1335 cps at 37° C.±0.2° C. was used.

A 10 part amount of the methyl cellulose and 0.17 parts of beclomethasone dipropionate were thoroughly mixed in a mortar and, then, the remaining hydroxypropyl cellulose was gradually added thereto. The resultant mixture was thoroughly mixed. Thereafter, 0.5 parts of stearic acid was added and thoroughly mixed.

Thus, a powdery composition for the application to the nasal cavity containing beclomethasone dipropionate uniformly dispersed therein was prepared. The powdery composition was filled in #2 hard gelatin capsules in an amount of 30 mg each to prepare a powdery preparation in a unit dosage form for the application to the nasal cavity.

Example 14

A powdery preparation in a unit dosage form for the application to the nasal cavity was prepared in the same manner as in Example 13, except that hydroxypropylmethyl cellulose having a viscosity of a 2% aqueous solution thereof of 20 cps at 37° C.±0.2° C. was used instead of the methyl cellulose. The powdery composition was filled in #2 hard gelatin capsules in an amount of 30 mg each to prepare a powdery preparation in a unit dosage form for the application to the nasal cavity.

Example 15

Powdery compositions were prepared in the same manner as in Example 12, except that the amounts of stearic acid were changed to 0, 0.01, 0.1, 0.3, 0.5, and 0.7 parts. These powdery compositions were filled in #2 hard gelatin capsules in an amount of 30 mg each.

The capsules thus prepared were allowed to stand at a temperature of 60° C. for one month. The residual percentages of beclomethasone dipropionate in the capsules were determined.

The results were as shown in Table 7.

TABLE 7

| Content of stearic acid (%) | 0 | 0.1 | 0.3 | 0.5 | 0.7 |
|---|---|---|---|---|---|
| Residual percentage of beclomethasone dipropionate (%) | 77.5 | 87.0 | 93.3 | 96.7 | 98.3 |

Example 16

The same evaluation test of Example 15 was carried out, except that palmitic acid was used instead of the stearic acid.

The result were as shown in Table 8.

TABLE 8

| Content of palmitic acid (%) | 0 | 0.1 | 0.3 | 0.5 | 0.7 |
|---|---|---|---|---|---|
| Residual percentage of beclomethasone dipropionate (%) | 78.5 | 92.0 | 93.8 | 96.2 | 98.1 |

Example 17

Powdery compositions were prepared in the same manner as in Example 12, except that the carboxymethyl cellulose was used, instead of the stearic acid in amounts of 0, 1, 2, and 3 parts. These powdery compositions were filled in #2 hard gelatin capsules in an amount of 30 mg each.

The capsules thus prepared were allowed to stand at a temperature of 60° C. for one month. The residual percentages of beclomethasone dipropionate in the capsules were determined.

The results were as shown in Table 9.

TABLE 9

| Content of carboxymethyl cellulose (%) | 0 | 1 | 2 | 3 |
|---|---|---|---|---|
| Residual percentage of beclomethasone dipropionate (%) | 82.6 | 92.1 | 93.2 | 95.8 |

Example 18

Powdery compositions were prepared in the same manner as in Example 13, except that the amounts of stearic acid were changed to 0, 0.01, 0.05, 0.1, and 0.5 parts. These powdery compositions were filled in #2 hard gelatin capsules in an amount of 30 mg each.

The capsules thus prepared were allowed to stand at a temperature of 60° C. for one month. The residual percentages of beclomethasone dipropionate in the capsules were determined.

The results were as shown in Table 10.

TABLE 10

| Content of stearic acid (%) | 0 | 0.05 | 0.1 | 0.5 |
|---|---|---|---|---|
| Residual percentage of beclomethasone dipropionate (%) | 75.5 | 90.2 | 92.3 | 96.8 |

Example 19

A 90 part amount of hydroxypropyl cellulose having a viscosity of a 2% aqueous solution of 1550 cps at 37° C.±0.2° C. and having a particle size such that 90% or more of the particles thereof had a particle diameter of 37 to 149 μm and 10 parts of dipotassium glycyrrhizinate were thoroughly mixed in a mixer. Then, 0.1, 0.3, 0.5, and 0.7 part of stearic acid were added to the resultant mixture to prepare powdery compositions for the application to the oral cavity.

The powdery compositions prepared above were filled into #2 gelatin hard capsules in an amount of 100 mg each. The capsules thus obtained were allowed to stand at a temperature of 60° C. for one month. The residual percentages of the glycyrrhizinate in the capsules were determined.

The results were as shown in Table 11.

TABLE 11

| Content of stearic acid (%) | 0 | 0.5 | 0.7 |
|---|---|---|---|
| Residual percentage of glycyrrhizinate (%) | 92.0 | 100 | 100 |

Example 20

A 100 part amount of hydroxypropyl cellulose having a viscosity of a 2% aqueous solution thereof of 1550 cps at 37° C.±0.2° C. and having a particle size such that 90% or more of the powder particles had a particle of 37 to 149 μm was used.

One part of the hydroxypropyl cellulose and 0.025 part of beclomethasone dipropionate were thoroughly mixed in a mortar and, then, 9 parts of hydroxypropyl cellulose were gradually mixed thereto. The resultant mixture was thoroughly mixed and, then, the remaining hydroxypropyl cellulose was added and thoroughly mixed in a mixer. Thereafter, 0.5 part of stearic acid was added and thoroughly mixed.

Thus, a powdery composition for the application to the oral cavity containing beclomethasone dipropionate uniformly dispersed therein was prepared. The powdery composition was filled in #2 hard gelatin capsules in an amount of 200 mg each to prepare a powdery preparation in a unit dosage form for the application to the oral cavity.

The capsules thus prepared were allowed to stand 60° C. for one month and at 40° C. for 6 months.

TABLE 12

| 60° C. | Storage period (day) | 7 | 14 | 21 | 30 |
|---|---|---|---|---|---|
| | Residual percentage of beclomethasone dipropionate (%) | 100.0 | 99.8 | 98.0 | 97.8 |
| 40° C. | Storage period (month) | 1 | 2 | 3 | 6 |
| | Residual percentage of beclomethasone dipropionate (%) | 100.0 | 99.0 | 98.7 | 97.5 |

Comparative Example 1

A 100 part amount of hydroxypropyl cellulose having a viscosity of 2% aqueous solution thereof of 1550 cps at 37° C.±0.2° C. and having a particle size such that 90% or more of the powder particles had a particle diameter of 37 to 149 μm was used.

One part of the hydroxypropyl cellulose and 0.025 part of beclomethasone dipropionate were thoroughly mixed in a mortar and, then, 9 parts of hydroxypropyl cellulose was gradually added thereto. The resultant mixture was thoroughly mixed and, then, the remaining hydroxypropyl cellulose were added and thoroughly mixed in a mixer. Thereafter, 0.5 part of ascorbic acid, which is different from unsaturated lower aliphatic monocarboxylic acid having six or less carbon atoms used in the present invention, was added and thoroughly mixed.

Thus, a powdery composition for the application to the oral cavity containing beclomethasone dipropionate uniformly dispersed therein was prepared. The powdery composition was filled in #2 hard gelatin capsules in an amount of 200 mg each to prepare a powdery preparation in a unit dosage form for the application to the oral cavity.

The capsules thus prepared were allowed to stand at a temperature of 60° C. for 30 days. The residual percentages of beclomethasone dipropionate in the capsules were determined.

The results were as shown in Table 13.

TABLE 13

| Storage period (day) | 7 | 14 | 21 | 30 |
|---|---|---|---|---|
| Residual % of beclomethasone dipropionate | 94.5 | 89.5 | 82.0 | 79.0 |

Comparative Example 2

A powdery preparation in a unit dosage form for the application to the oral cavity was prepared in the same manner as in Comparative Example 1, except that glutamic acid, which is different from aliphatic polycarboxylic acid used in the present invention, was used instead of the ascorbic acid.

The capsules obtained above were allowed to stand at a temperature of 60° C. for 30 days. The residual percentages of the beclomethasone dipropionate in the capsules were determined.

The results were as shown in Table 14.

TABLE 14

| Storage period (day) | 7 | 14 | 21 | 30 |
|---|---|---|---|---|
| Residual % of beclomethasone dipropionate | 95.5 | 91.2 | 88.5 | 83.2 |

Comparative Example 3

A powdery preparation in a unit dosage form for the application to the oral cavity was prepared in the same manner as in Comparative Example 1, except that sodium carboxymethyl cellulose having carboxylate groups different from carboxyl groups and used instead of the ascorbic acid.

The capsules obtained above were allowed to stand at a temperature of 60° C. for 30 days. The residual percentages of the beclomethasone dipropionate in the capsules were determined.

The results were as shown in Table 15.

TABLE 15

| Storage period (day) | 7 | 14 | 21 | 30 |
|---|---|---|---|---|
| Residual % of beclomethasone dipropionate | 93.0 | 86.2 | 80.0 | 75.1 |

Comparative Example 4

A powdery preparation in a unit dosage form for the application to the oral cavity was prepared in the same manner as in Comparative Example 1, except that aspirin, which is different from steroid or glycyrrhizic acid type anti-inflammatory agents used in the present invention, was used instead of beclomethasone dipropionate and stearic acid, which is used as a stabilizer in the present invention, was used instead of the ascorbic acid.

The capsules obtained above were allowed to stand at a temperature of 60° C. for 30 days. The residual percentages of the aspirin in the capsules were determined.

The results were as shown in Table 16.

TABLE 16

| Storage period (day) | 7 | 14 | 21 | 30 |
|---|---|---|---|---|
| Residual % of aspirin | 92.2 | 85.5 | 78.2 | 72.0 |

Comparative Example 5

A powdery preparation in a unit dosage form for the application to the oral cavity was prepared in the same manner as in Comparative Example 1, except that azulen, which is different from steroid or glycyrrhizic acid type anti-inflammatory agents used in the present invention, was used instead of the beclomethasone dipropionate and palmitic acid, which is used as a stabilizer in the present invention, was used instead of the ascorbic acid.

The capsules obtained above were allowed to stand at a temperature of 60° C. for 30 days. The residual percentages of the azulen in the capsules were determined.

The results were as shown in Table 17.

TABLE 17

| Storage period (day) | 7 | 14 | 21 | 30 |
|---|---|---|---|---|
| Residual % of azulen | 92.0 | 81.5 | 74.2 | 65.5 |

Comparative Example 6

A powdery preparation in a unit dosage form for the application to the oral cavity was prepared in the same manner as in Comparative Example 1, except that magnesium stearate, which is different from stearic acid used in the present invention, was used instead of the ascorbic acid.

The capsules obtained above were allowed to stand at a temperature of 60° C. for 30 days. The residual percentages of the beclomethasone dipropionate in the capsules were determined.

The results were as shown in Table 18.

TABLE 18

| Storage period (day) | 7 | 14 | 21 | 30 |
|---|---|---|---|---|
| Residual % of beclomethasone dipropionate | 94.3 | 90.5 | 85.4 | 80.4 |

Comparative Example 7

A 100 part amount of hydroxypropyl cellulose having a viscosity of a 2% aqueous solution thereof of 1550 cps and having a particle size distribution such that 90% or more of the powder particles had a particle diameter of 37 to 149 $\mu$m was used.

A 10 part amount of the hydroxypropyl cellulose and 0.17 part of beclomethasone dipropionate were thoroughly mixed in a mixer and, then, the remaining hydroxypropyl cellulose was added thereto, followed by mixing. Thereafter, 0.5 part of ascorbic acid was added and thoroughly mixed. Thus, a powdery pharmaceutical composition for the application to the nasal cavity containing beclomethasone dipropionate uniformly dispersed therein was prepared.

The powdery composition obtained above was filled in #2 hard gelatin capsules in an amount of 30 mg each to prepare a powdery preparation in a unit dosage form for the application to the nasal cavity.

The residual percentages of the beclomethasone dipropionate were determined by allowing the capsules to stand at a temperature of 60° C. for 30 days.

The results were as shown in Table 19.

TABLE 19

| Storage period (day) | 7 | 14 | 21 | 30 |
|---|---|---|---|---|
| Residual % of beclomethasone dipropionate | 93.6 | 90.1 | 82.2 | 79.1 |

Comparative Example 8

A powdery preparation in a unit dosage form for the application to the nasal cavity was prepared in the same manner as in Comparative Example 7, except that glutamic acid was used instead of the ascorbic acid.

The capsules obtained above were allowed to stand at a temperature of 60° C. for 30 days. The residual percentages of the beclomethasone dipropionate in the capsules were determined.

The results were as shown in Table 20.

TABLE 20

| Storage period (day) | 7 | 14 | 21 | 30 |
|---|---|---|---|---|
| Residual % of beclomethasone dipropionate | 93.5 | 89.2 | 85.5 | 80.2 |

Comparative Example 9

A powdery preparation in a unit dosage form for the application to the nasal cavity was prepared in the same manner as in Comparative Example 7, except that aspirin was used instead of beclomethasone dipropionate and stearic acid was used instead of the ascorbic acid.

The capsules obtained above were allowed to stand at a temperature of 60° C. for 30 days. The residual percentages of the aspirin in the capsules were determined.

The results were as shown in Table 21.

TABLE 21

| Storage period (day) | 7 | 14 | 21 | 30 |
|---|---|---|---|---|
| Residual % of aspirin | 94.2 | 87.2 | 80.5 | 75.1 |

Comparative Example 10

A powdery preparation in a unit dosage form for the application to the oral cavity was prepared in the same manner as in Comparative Example 7, except that magnesium stearate was used instead of the ascorbic acid.

The capsules obtained above were allowed to stand at a temperature of 60° C. for 30 days. The residual percentages of the beclomethasone dipropionate in the capsules were determined.

The results were as shown in Table 14.

TABLE 22

| Storage period (day) | 7 | 14 | 21 | 30 |
|---|---|---|---|---|
| Residual % of beclomethasone dipropionate | 95.3 | 91.5 | 86.4 | 81.5 |

Example 21

A 100 part amount of hydroxypropyl cellulose having a viscosity of a 2% aqueous solution thereof of 1550 cps at 37° C.±0.2° C. and having a particle size such that 90% or more of the powder particles had a particle diameter of 37 to 149 μm was used.

A 10 part amount part of the hydroxypropyl cellulose and 0.17 part of beclomethasone dipropionate were thoroughly mixed in a mixer and, then, the remaining hydroxypropyl cellulose was gradually added thereto. The resultant mixture was thoroughly mixed. Thereafter, 0.5 part of stearic acid was added and thoroughly mixed.

Thus, a powdery composition for the application to the nasal cavity containing beclomethasone dipropionate uniformly dispersed therein was prepared. The powdery composition was filled in #2 hard gelatin capsules in an amount of 30 mg each to prepare a powdery preparation in a unit dosage form for the application to the nasal cavity.

The capsules thus prepared were allowed to stand at a temperature of 60° C. for 30 days or at 40° C. for 6 month. The residual percentages of beclomethasone dipropionate in the capsules were determined.

The results were as shown in Table 23.

TABLE 23

| 60° C. | Storage period (day) | 7 | 14 | 21 | 30 |
|---|---|---|---|---|---|
| | Residual % of beclomethasone dipropionate | 99.0 | 98.7 | 98.0 | 96.7 |
| 40° C. | Storage period (month) | 1 | 2 | 3 | 6 |
| | Residual % of beclomethasone dipropionate | 99.9 | 99.5 | 99.0 | 98.0 |

Comparative Example 11

A powdery preparation for the application to the oral cavity in the same manner as in Example 1, except that capric acid (i.e., a saturated higher aliphatic monocarboxylic acid having 10 carbon atoms) was used instead of the stearic acid.

However, the powdery preparation obtained above was not appropriate as a powdery preparation because, when the powdery preparation filled in the capsule was administered to the oral cavity by the above-explained spraying device, the odor was too strong.

Example 22

A 100 part amount of hydroxypropyl cellulose having a viscosity of a 2% aqueous solution thereof of 1550 cps at 37° C.±0.2° C. and having a particle size such that 90% or more of the powder particles had a particle diameter of 37 to 149 μm was used.

A 10 part amount part of the hydroxypropyl cellulose and 1.7 parts of triamcinolone acetonide were thoroughly mixed in a mixer and, then, the remaining hydroxypropyl cellulose was gradually added thereto. The resultant mixture was thoroughly mixed. Thereafter, 0.5 part of stearic acid and 0.3 part of magnesium stearate were added and thoroughly mixed. Thus, a powdery composition for the application to the nasal cavity containing triamcinolone acetonide uniformly dispersed therein was prepared.

The powdery composition obtained above was pulverized by a coarse grinding machine and, then, compressed to prepare tablets having a Monsanto hardness of 3 to 4 kg. The tablets were pulverized by the grinding machine to prepare the powder particles. The powder particles thus obtained were sieved to obtain the powder particles having a particle size of 60 to 400 meshes. The powder particles were, then, filled in #2 hard gelatin capsules in an amount of 30 mg each to prepare a powdery preparation in a unit dosage form for the application to the nasal cavity.

Example 23

A 100 part amount of hydroxypropyl cellulose having a viscosity of a 2% aqueous solution thereof of 1550 cps at 37° C.±0.2° C. and having a particle size such that 90% or more of the powder particles had a particle diameter of 37 to 149 μm was charged into a fluidized bed type granulator. Then, 50 parts of, ethanol mixture containing 0.025 part of beclomethasone dipropionate and 5 parts of hydroxypropyl cellulose having a viscosity of a 2% aqueous solution thereof of 7 cps at 37° C.±0.2° C. dissolved therein and also containing 0.5 part of stearic acid dissolved therein were sprayed from the spraying nozzle of the granulator, followed by drying. Thus, the powder particles impregnated with the solid components in the ethanol mixture was obtained. The powder particles were sieved to obtain those having a particle size of 60 to 400 meshes. The powder particles thus obtained were filled in #2 hard gelatin capsules in an amount of 200 mg each to prepare a powdery preparation in a unit dosage form for the application to the oral cavity.

Example 24

A 80 part amount of hydroxypropyl cellulose having a viscosity of a 2% aqueous solution thereof of 1550 cps at 37° C.±0.2° C. and having a particles size such that 90% or more of the powder particles had a particle diameter of 37 to 149 μm and 1000 parts of an ethanol suspension containing 0.2 part of the dissolved beclomethasone dipropionate and 0.4 part of the suspended stearic acid were casted on the surface of releasing paper. After drying, the casted film was obtained.

The film obtained above was ground and pulverized by a grinding machine and, then, sieved to the powder particles having a particle size of 60 to 400 meshes. The powder particles were filled in #2 hard gelatin capsules in an amount of 200 mg each to prepare a powdery preparation in a unit dosage form for the application to the oral cavity.

We claim:

1. A powdery pharmaceutical composition for application to the mucosa of the oral or nasal cavity comprising:
   (a) a base selected from the group consisting of lower alkyl ethers of cellulose;
   (b) a pharmaceutically effective amount of a drug selected from the group consisting of steroidal anti-inflammatory agents or glycyrrhizic acid anti-inflammatory agents; and
   (c) a stabilizer for the drug in the form of at least one low irritant solid organic acid selected from the group consisting of saturated higher aliphatic monocarboxylic acids having 12 to 24 carbon atoms, aliphatic hydrocarbon dicarboxylic acids having 4 to 6 carbon atoms, hydroxyl aliphatic hydrocarbon di- or tricarboxylic acids having 4 to 8 carbon atoms, benzoic acid and its derivatives, unsaturated lower aliphatic monocarboxylic acids having six or less carbon atoms, and carboxymethyl cellulose and carboxymethylethyl cellulose, said stabilizer being present in an amount of 0.05% to 5% by weight in the composition.

2. A powdery pharmaceutical composition as claimed in claim 1, wherein at least about 90% by weight of the stabilizer particles has an effective particle diameter of about 75 μm or less.

3. A powdery pharmaceutical composition for application to the mucosa of the oral cavity as claimed in claim 1, wherein said stabilizer is at least one member selected from the group consisting of saturated higher aliphatic monocarboxylic acids having 12 to 24 carbon atoms, aliphatic dicarboxylic acids having 4 to 6 carbon atoms, hydroxy aliphatic hydrocarbon di- or tricarboxylic acids having 4 to 8 carbon atoms, benzoic acid and its derivatives, and carboxymethyl cellulose and carboxymethylethyl cellulose.

4. A powdery pharmaceutical composition for application to the mucosa of the nasal cavity as claimed in claim 1, wherein said stabilizer is a saturated higher aliphatic monocarboxylic acid having 12 or more carbon atoms or a cellulose derivative having carboxyl groups.

5. A powdery pharmaceutical composition as claimed in claim 1, wherein said saturated higher aliphatic hydrocarbon monocarboxylic acid is stearic acid, palmitic acid, lauric acid, or myristic acid.

6. A powdery pharmaceutical composition as claimed in claim 1, wherein said aliphatic hydrocarbon dicarboxylic acid is succinic acid, fumaric acid, or maleic acid.

7. A powdery pharmaceutical composition as claimed in claim 1, wherein said hydroxy aliphatic hydrocarbon di- or tricarboxylic acid is tartaric acid or citric acid.

8. A powdery pharmaceutical composition as claimed in claim 1, wherein said benzoic acid and its derivatives is benzoic acid, parahydroxybenzoic acid, or salicylic acid.

9. A powdery pharmaceutical composition as claimed in claim 1, wherein said steroid type anti-inflammatory agent is beclomethasone dipropionate, betamethasone, betamethasone valerate, triamcinolone, triamcinolone acetonide, dexamethasone, fluocinolone acetonide, fluocinonide, flumethasone, hydrocortisone, prednisolone, or prednisone.

10. A powdery pharmaceutical composition as claimed in claim 1, wherein the moisture content of the lower alkyl ether of cellulose is within the range of from 3% to 9% by weight.

11. A powdery pharmaceutical composition as claimed in claim 1, wherein said lower alkyl ether of cellulose is hydroxypropyl cellulose, methyl cellulose, or hydroxypropyl methyl cellulose.

12. A powdery pharmaceutical composition as claimed in claim 1, wherein at least about 90% by weight of the powder particles of the pharmaceutical composition has an effective particle diameter of about 20 to 250 μm.

13. A powdery pharmaceutical preparation in unit dosage form for application to the mucosa of the oral or nasal cavity comprising the powdery pharmaceutical composition of claim 1.

14. A powdery pharmaceutical preparation as claimed in claim 13, wherein said pharmaceutical composition is filled in a capsule.

15. A powdery pharmaceutical composition as claimed in claim 1, wherein the drug is a glycyrrhizic acid anti-inflammatory agent.

16. A powdery pharmaceutical composition as claimed in claim 15, wherein said glycyrrhizic acid anti-inflammatory agent is glycyrrhizic acid, disodium glycyrrhizinate, trisodium glycyrrhizinate, monopotassium glycyrrhizinate, dipotassium glycyrrhizinate or monoammonium glycyrrhizinate.

17. A powdery pharmaceutical composition as claimed in claim 1, wherein said base is present in an amount of 89.374% to 99.925% by weight in the composition.

18. A method for preparing a powdery pharmaceutical composition for application to the mucosa of the oral or nasal cavity, comprising the step of mechanically mixing:

(a) a base selected from the group consisting of lower alkyl ethers of cellulose;

(b) a pharmaceutically effective amount of a drug selected from the group consisting of steroidal anti-inflammatory agents or glycyrrhizic acid anti-inflammatory agents; and (c) a stabilizer for the drug in the form of at least one low irritant solid organic acid selected from the group consisting of saturated higher aliphatic monocarboxylic acids having 12 to 24 carbon atoms, aliphatic hydrocarbon dicarboxylic acids having 4 to 6 carbon atoms, hydroxy aliphatic hydrocarbon di- or tricarboxylic acids having 4 to 8 carbon atoms, benzoic acid and its derivatives, unsaturated lower aliphatic monocarboxylic acids having six or less carbon atoms, and carboxymethyl cellulose and carboxymethylethyl cellulose, said stabilizer being present in an amount of 0.05% to 5% by weight in the composition.

19. A method as claimed in claim 18, wherein the mixed composition is compressed under pressure and, then, the compressed mixture is pulverized.

20. A method for preparing a powdery pharmaceutical composition for application to the mucosa of the oral or nasal cavity, comprising the steps of:

impregnating the lower alkyl ethers of cellulose with a solution or dispersion, in an organic solvent, of a pharmaceutically effective amount of a drug selected from the group consisting of steroidal anti-inflammatory agents or glycyrrhizic acid anti-inflammatory agents and a stabilizer for the drug in the form of at least one low irritant solid organic acid selected from the group consisting of saturated higher aliphatic monocarboxylic acids having 12 to 24 carbon atoms, aliphatic hydrocarbon dicarboxylic acids having 4 to 6 carbon atoms, hydroxy aliphatic hydrocarbon di- or tricarboxylic acids having 4 to 8 carbon atoms, benzoic acid and its derivatives, unsaturated lower aliphatic monocarboxylic acids having six or less carbon atoms, and carboxymethyl cellulose and carboxymethylethyl cellulose, said stabilizer being present in an amount of 0.05% to 5% by weight in the composition, and drying the impregnated product.

21. A method for preparing a powdery pharmaceutical composition for application to the mucosa of the oral or nasal cavity comprising the steps of:

dissolving or dispersing, in an organic solvent, water, or the mixture thereof (a) the lower alkyl ethers of cellulose, (b) a pharmaceutically effective amount of a drug selected from the group consisting of steroidal anti-inflammatory agents or glycyrrhizic acid anti-inflammatory agents, and (c) a stabilizer for the drug in the form of at least one low irritant solid organic acid selected from the group consisting of saturated higher aliphatic monocarboxylic acids having 12 to 24 carbon atoms, aliphatic hydrocarbon dicarboxylic acids having 4 to 6 carbon atoms, hyroxy aliphatic hydrocarbon di- or tricarboxylic acids having 4 to 8 carbon atoms, benzoic acid and its derivatives, unsaturated lower aliphatic monocarboxylic acids having six or less carbon atoms, and carboxymethyl cellulose and carboxymethylethyl cellulose, said stabilizer being present in an amount of 0.05% to 5% by weight in the composition, evaporating the organic solvent, water, or the mixture thereof from the resultant solution or dispersion; and pulverizing the evaporated product.

22. A method for stabilizing a powdery pharmaceutical composition containing a steroidal anti-inflammatory agent or glycyrrhizic acid anti-inflammatory agent for application to the mucosa of the oral or nasal cavity, comprising incorporating at least one low irritant solid organic acid selected from the group consisting of saturated higher aliphatic monocarboxylic acids having 12 to 24 carbon atoms, aliphatic hydrocarbon dicarboxylic acids having 4 to 6 carbon atoms, hydroxy aliphatic hydrocarbon di- or tricarboxylic acids having 4 to 8 carbon atoms, benzoic acid and its derivatives, unsaturated lower aliphatic monocarboxylic acids having six or less carbon atoms, and carboxymethyl cellulose and carboxymethylethyl cellulose into a mixture of lower alkyl ethers of cellulose and a pharmaceutically effective amount of a drug selected from the group consisting of said steroidal anti-inflammatory agent or glycyrrhizic acid anti-inflammatory agents, said at least one low irritant solid organic acid being a stabilizer for the drug and being present in an amount of 0.05% to 5% by weight of the composition.

* * * * *